Figure 1:
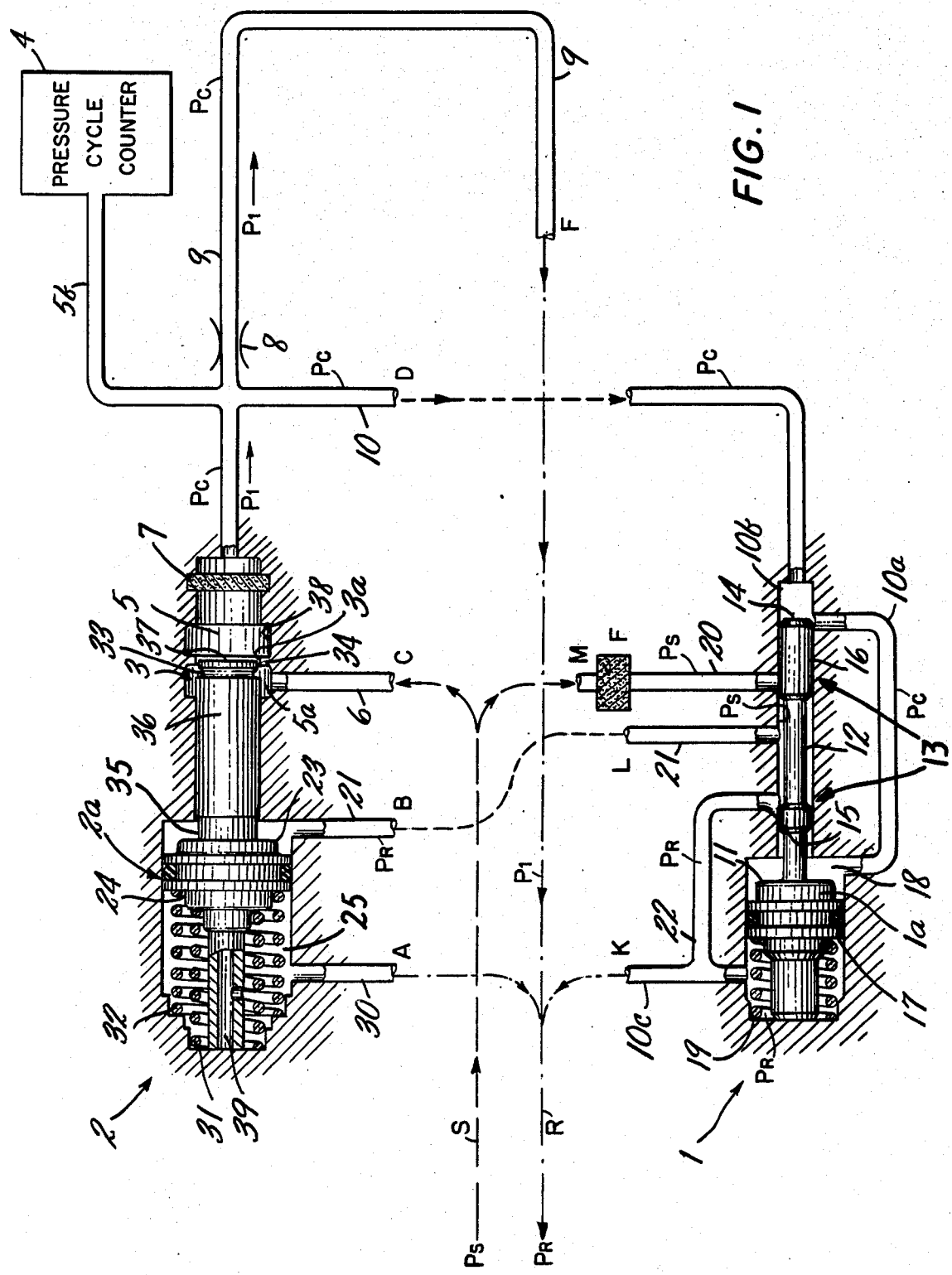

United States Patent [19]

Lanctot et al.

[11] Patent Number: 4,468,954

[45] Date of Patent: Sep. 4, 1984

[54] DEVICE FOR DETERMINING THE CONCENTRATION OF SUSPENDED SOLID CONTAMINANTS IN A FLUID

[75] Inventors: Robert Lanctot, St. Petersburg, Fla.; Bernard F. Silverwater, Plainview, N.Y.

[73] Assignee: Pall Corporation, Glen Cove, N.Y.

[21] Appl. No.: 443,360

[22] Filed: Nov. 22, 1982

[51] Int. Cl.³ .............................................. G01N 15/06
[52] U.S. Cl. ..................................... 73/61 R; 340/627
[58] Field of Search .................... 73/61 R, 61.1 R, 54, 73/55; 340/607, 627

[56] References Cited

U.S. PATENT DOCUMENTS 3,267,723 8/1966 Robinson .............................. 73/61 R
3,357,236 12/1967 Kasten ................................. 73/61 R Primary Examiner—S. Clement Swisher
Assistant Examiner—Hezron Williams

[57] ABSTRACT

A device is provided for determining the density or concentration of solid contaminants suspended in a fluid, having an orifice or narrow passage through which the fluid carrying suspended solid contaminants is passed, and monitoring the rate of build-up of the contaminants at the orifice or narrow passage as a function of the density or concentration of the contaminants in the fluid.

6 Claims, 2 Drawing Figures

U.S. Patent    Sep. 4, 1984    Sheet 1 of 2    4,468,954

DEVICE FOR DETERMINING THE CONCENTRATION OF SUSPENDED SOLID CONTAMINANTS IN A FLUID von Alfthan U.S. Pat. No. 3,359,786, patented Dec. 26, 1967, provides a method and apparatus for determining the shives content of a fluid pulp fiber suspension. The fiber suspension is fed through a slit having a predetermined size, such that shives or fiber bundles above a predetermined maximum size are caught by the slit. The build-up of the material caught by the slit decreases the rate of liquid flow through the slit, and the decrease in flow rate is determined by rinsing the slit as soon as it has been clogged to a predetermined extent, comparing the number of rinsings of the slit per unit time with a pulp fiber suspension of known fiber content, and then from these results determining the content of shives or fiber bundles in the suspension.

In the device shown in the drawings, the annular slit 10 is variable in dimensions according to the position of the spherical body 9, which is supported by a pneumatic cylinder 13. The size of the slit is so adjusted in relation to flow as to maintain a selected fluid level in the tube 7. As the slit blocks, flow diminishes and the fluid level rises. Eventually, the fluid level reaches the contact 18, which actuates a signal and opens the slit to clean it out. This cycle is repeated over and over again as the slit plugs up, until the entire pulp quantity has flowed through the apparatus. At the same time, the number of cycles is recorded on a counter. The number of cycles indicated by the counter serves as a measure of the shives content of the pulp. The device can also be operated continuously, in which case the number of rinsings per unit time is recorded and serves as a measure of the shives content.

Molten liquid metals, particularly alkali metals such as sodium, can tolerate small amounts of impurities but not large amounts. Molten sodium, for example, can contain some sodium oxide, but sodium oxide is detrimental for various reasons. A device has accordingly been developed called a "plugging meter" whose plugging temperature is dependent on the temperature/solubility relation of sodium oxide in molten sodium. Sodium flowing through a section of pipe with a flow restriction, such as a perforated plate or orifice, is cooled upstream of the plate until the temperature reaches a value such that the oxide content precipitates, collects upon, and eventually plugs the orifice. The plugging temperature corresponds to a certain oxide concentration, which can be determined by referring to a calibration curve relating oxide concentration to plugging temperature. Plugging meters of this type are described in U.S. Pat. Nos. 3,222,916 to Davis, patented Dec. 14, 1965, and 4,178,795 to Nagai, patented Dec. 18, 1979. These devices are temperature-dependent for plugging.

Kasten U.S. Pat. No. 3,357,236, patented Dec. 12, 1967, provides a contamination indicator used to measure the amount of solid and water contaminants in fuel. The system has two filter units in series flow relation, one of which removes only solid contaminants and the other of which removes only water from the fuel flowing therethrough. Two identical contamination indicators are provided, one connected to the filter removing solid contaminants and the other connected to the filter removing water. These indicators measure the rate of differential pressure increase across each of the filter units, and determine the concentration of the solid and/or water contamination in terms of the increase in pressure differential across the filter, based on the principle that the build-up on the filter is proportional to the concentration.

Isley and Dodd U.S. Pat. No. 4,263,805, patented Apr. 28, 1981, provide a device for detecting the presence of solid impurities in a pressurized fluid. The device comprises a housing with a fluid passageway open to the pressurized fluid at one end and at the other end to a low pressure fluid region via a restricted port. A filter strip is disposed across and obstructs the fluid flow through the passageway, thereby removing solid or liquid particles from liquid flowing through the passageway. A differential pressure-sensing means communicates with the fluid passageway, and detects the differential pressure across the strip. The degree of clogging of the strip is used as an indication of the presence of impurities within the fluid and the proportion or amount, and when the pressure drop across the filter element reaches a predetermined value, a differential pressure transducer is tripped, and generates appropriate signals to an indicating means, which in turn signals the operator, who can then service the filter.

Robinson U.S. Pat. No. 3,267,723, patented Aug. 23, 1966, provides a device for determining the presence of contaminants in hydraulic system fluids. The device is attached to the hydraulic pressure and return lines of the system to be examined, and traps a sample of the hydraulic fluid, which is flushed with a filtered solvent and filtered through a fluid monitor containing a filter patch. The patch is dried and compared with an acceptable standard filter patch, using a magnifier to determine the build-up of material on the filter and thereby the contaminant concentration in the fluid, in an approximate way, and thus make certain that the contamination load does not exceed a predetermined maximum limit.

In accordance with the invention, a device is provided for determining the density or concentration of solid contaminants suspended in a fluid, having an orifice or narrow passage through which the fluid carrying suspended solid contaminants is padded, and monitoring the rate of build-up of the solid contaminants at the orifice or narrow passage as a function of the density or concentration of the contaminants in the fluid.

The contaminant sensing and monitoring device in accordance with the invention comprises, in combination:

(1) a housing having a fluid inlet and a fluid outlet for attachment respectively to a system supply fluid line and a system return fluid line;

(2) a fluid passage through the housing extending between the fluid inlet and the fluid outlet;

(3) a first flow restriction across the fluid passage, sized to prevent passage therethrough of solid contaminant particles to be sensed and estimated, and suspended in fluid flowing through the restriction, and collect such particles upstream thereof;

(4) a second flow restriction across the fluid passage, downstream of the first and controlling fluid flow through the passage and the first flow restriction to less than a selected maximum;

(5) first valve means movable only between first and second positions, having a first pressure receiving surface selectively exposed to system return pressure or to fluid pressure downstream of the first flow restriction and a second pressure receiving surface exposed solely to system return fluid pressure;

(6) first biasing means biasing the first valve means towards the second position against fluid pressure downstream of the first flow restriction, the valve means being moved into the first position against the biasing force whenever fluid pressure downstream of the flow restriction is greater than system return fluid pressure; and otherwise being moved into the second position under the biasing force;

(7) second valve means movable only between first and second positions having first and second pressure-receiving surfaces exposed, respectively, to either system supply or system return fluid pressure, according to the position of the first valve means, and fluid pressure downstream of the first flow restriction; and to system return fluid pressure;

(8) second biasing means biasing the second valve means towards the second position against system supply or system return fluid pressure and fluid pressure downstream of the first flow restriction; the valve means being moved into the first position whenever system supply fluid pressure and/or fluid pressure downstream of the first flow restriction greater than system return fluid pressure is applied to the first pressure-receiving surface of the second valve means and otherwise being moved into the second position under the biasing force;

(9) the first valve means controlling application of system supply fluid pressure to the first pressure-receiving surface of the second valve means, and permitting such application only when in the first position; whereby the first and second valve means each are moved against the biasing forces of their respective biasing means into their first positions while the first flow restriction remains in a relatively contaminant-unblocked condition, and whenever the flow becomes blocked by contaminants and the fluid pressure differential thereacross exceeds a predetermined minimum, both valve means move into their second positions under the biasing forces of their respective biasing means;

(10) means for cleaning away contaminants collected at the first flow restriction and restoring it to a contaminant-unblocked condition whenever the second valve means is in the second position; and

(11) means responsive to fluid pressure differential between system return fluid pressure and fluid pressure downstream of the first flow restriction for signalling each time such fluid pressure differential falls below a predetermined value.

In a preferred embodiment, means such as a diagnostic filter is provided downstream of the first flow restriction to collect any particulate contaminants passing from the first flow restriction after it goes through an automatic cleaning cycle.

The first and second valve means are preferably slide spool or poppet valves, or a combination thereof, spring-biased into one of their two limiting positions, and exposed to fluid pressure on each side thereof, so as to be moved against the spring bias at a predetermined pressure differential thereacross. The bias means can also be a magnet or a combination of magnets and magnetic elements.

The means for signalling the blocking cycles of the silt trap can take the form of a mechanical or magnetic differential pressure indicator, or of a counter, and can be arranged to give a visual signal, or to give an electric signal, such as light a light or sound an alarm, or to make a mechanical record, such as recording the cycling time on a time graph, at the end of each cycle.

The device requires some flow through the silt trap, but this can be metered to be a function of the pressure of the main flow. All other components are pressure-responsive, and so no flow but only pressure communication is required for their operation.

Figure 2:
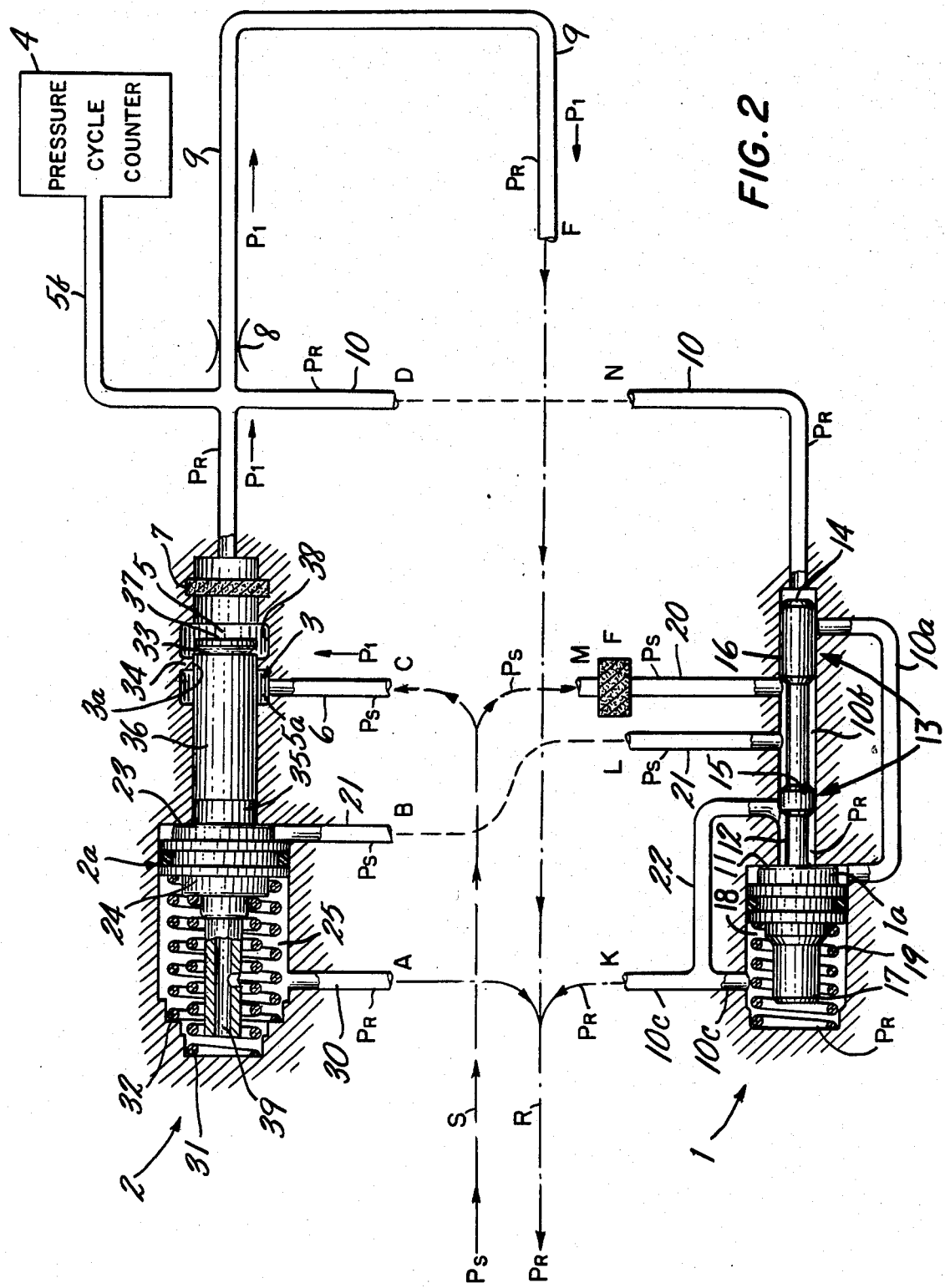

A preferred embodiment of the device of the invention is shown in the drawings, in which:

FIG. 1 is a flow diagram showing the flow circuit of the device in accordance with the invention, with each of the first and second valve means in the first position, and the first flow restriction or silt trap at the beginning of a cycle in relatively contaminant-unblocked condition; and FIG. 2 represents a flow diagram with each of the first and second valve means in the second position, and the silt trap after reaching a relatively contaminant-blocked condition in position for dumping its contaminant load.

The device shown in FIGS. 1 and 2 has a supply fluid line S with internal fluid pressure $P_s$ in fluid flow connection at inlet port C and a return fluid line R with internal fluid pressure $P_r$ in fluid flow connection with outlet port F.

In this device the first valve means is the toggle valve 1, and the second valve means is the dirt sensor valve 2. The first flow restriction is the silt trap 3. Whenever the silt trap 3 is blocked by contaminants, the fluid pressure downstream $(P_c)$ is reduced, and whenever $P_c$ is sufficiently less than supply line pressure $P_s$ that the fluid pressure differential $\Delta(P_c-P_r)$ reaches a predetermined value, corresponding to a certain degree of clogging of the silt trap 3, the sensor valve 2 will be actuated by its spring and shut off.

Downstream of the silt trap 3 is a diagnostic filter 7, for collecting any particulate contaminants passing downstream of the silt trap during each cycle. Thence, fluid line 5 extends past the flow controlling orifice 8 to the line 9.

A side line 5b leads to a pressure cycle counter 4, which counts the clogging/cleaning cycles of the silt trap 3 according to pressure changes in line 5.

Thus, the path P1 for fluid flow through the device (representing, in most instances, only a small proportion of the full flow in the fluid system) enters the device at the port C, proceeds via line 6 to and through the silt trap 3, and then along the fluid passageway 5 past the second flow restriction 8, the flow controlling orifice, thence proceeding by way of line 9 to the exit port F and line R.

The flow controlling orifice 8 is adjustable, and controls the flow rate through this path P1, which of course also determines the silting-up rate at silt trap 3, and thus the cycling time for each clogging interval. In the device shown in the drawing, the flow in path P1 is 14 cc per minute, but this flow rate may be adjusted upwardly or downwardly, simply by increasing or diminishing the size of the flow restriction 8.

The toggle valve 1 is in fluid pressure-sensing connection with the fluid passageway 5 between the silt trap 3 and the flow controlling orifice 8 by way of the passage 10, which bifurcates into 10a, 10b and which communicates via 10a fluid pressure $P_c$ downstream of the silt trap 3 with the upstream pressure-receiving face 11 of the toggle valve piston 1a, whenever the spool valve 13 is in its first position, as shown in FIG. 1, but not otherwise.

Fixedly attached to the valve and projecting outwardly from the upstream surface 11 is a valve stem 12 carrying a spool valve 13, whose spools 15, 16 slidingly reciprocate along the passage 10b with movement of the toggle valve piston 1a. The upstream pressure surface 14 of spool 16 receives pressure $P_c$ via passage 10 in all positions of the valve 13.

Another bifurcated passage 10c communicates the downstream side of the piston 1a via port K with the return line R, so as to communicate return line pressure $P_r$ to the downstream face 17 of the toggle valve piston 1a.

Extending laterally from the passage 10b with flow therethrough controlled by the spool valve 13 are three passages 20, 21, and 22. Passage 20 is in fluid pressure connection via inlet port M and filter F with the supply line S. Passage 21 is in fluid pressure connection via ports L and B with the upstream face 23 of the dirt sensor valve piston 2a in valve chamber 25. The third passage 22 extends to the passageway 10c, which in turn is in fluid pressure communication via port K with the return line R, and return line pressure $P_r$.

With the spool valve 13 in the first position, as shown in FIG. 1, passages 21 and 22 are in fluid pressure communication, so that return line pressure $P_r$ is communicated to the upstream face 23 of the dirt sensor valve piston 24. With the spool valve 13 in its second limiting position, as shown in FIG. 2, the spool valve communicates passages 20, 21, with the result that the upstream surface of the dirt sensor valve now senses supply line pressure $P_s$.

The toggle valve piston 1a reciprocates in valve chamber 18, in the downstream portion of which the compression spring 19 is arranged to bias the toggle valve into the second position shown in FIG. 2. The biasing force of the spring is low enough, however, that whenever the pressure $P_c$ downstream of the silt trap 3 is either equal to supply line pressure $P_s$ or some selected value less than that, 80% of $P_s$ pressure for example, communicated to only the upstream surface 14 of the spool valve 13, the biasing force of the spring is overcome, and the toggle valve moves to the left, into its first position, shown in FIG. 1. In this position $P_c$ pressure is also applied to upstream surface 11. Whenever however the pressure $P_c$ in passages 10, 10a upstream of the piston 1a is diminished sufficiently that the biasing force of the spring taken together with return line pressure $P_r$ applied to the downstream face 17 of the piston 1a can overcome the pressure on the upstream surface 11 and 14, the toggle valve will be moved to the right, into its second limiting position, shown in FIG. 2. In this position, the spool valve 13 via spool 15 closes off communication of passages 21, 22, and via spool 16 closes off communication of passages 10, 10a, and communicates passage 22 with the upstream face 11 of piston 1a, thus equalizing pressure on each side of the valve, and communicates supply line pressure $P_s$ to the upstream surface 23 of the dirt sensor valve piston 2a instead of return line pressure $P_r$.

The passageway 30 communicates the downstream pressure face 24 of the dirt sensor valve piston 2a via port A with return line pressure $P_r$ in the return line R. The valve chamber 25 on the downstream side of valve piston 2a carries two compression springs 31, 32 biasing the dirt sensor valve piston 2a to the right, towards its second position, as shown in FIG. 2. Two springs are used for convenience of packaging using standard "off the shelf springs", but one larger spring can be used. The combined biasing force of the springs and return line pressure $P_r$ is insufficient to overcome the opposing force of supply line pressure $P_s$ whenever this is applied individually to the upstream surface 23 of the valve piston via passages 21, or of $P_c$ whenever this is at least equal to 20% of $P_s$, applied individually to pressure receiving surface 37 of the spool valve 36, so that whenever either one of these conditions exists the valve is driven to the left, into its first position, as shown in FIG. 1.

The dirt sensor valve piston 2a has a valve stem 35 with a spool valve 36 attached, reciprocating in a sliding movement between limiting positions. The silt trap 3 is formed at a narrow annular gap 3a defined between the internal diameter at the end 34 of the valve bore and the valve spool outer diameter at 37. The silt collects in the recess 33 just before the gap and in the trap between end 34 and spool diameter 37.

Thus, under supply line pressure $P_s$ at face 23 and with $P_c$ at face 37, the dirt sensor valve piston 2a is driven to the left, into its first position, as shown in FIG. 1, with the gap 3a open, overcoming downstream return line pressure and the biasing force of the springs. Whenever the spool valve 13 of valve 1 is in the first position shown in FIG. 1, passages 21, 22 communicate return line pressure $P_r$ to the upstream valve face 23, thus equalizing pressure on each side of the valve, but while $P_c$ is high enough, valve 2 will be in its first position, to the left, as shown in FIG. 1. When $P_c$ diminishes sufficiently that the biasing force of springs 31, 32 can overcome the force due to $P_c$ on surface 37, the valve piston 1a is driven to the right, into its second position, as shown in FIG. 2.

The operation of the valve is accordingly as follows: The unit is connected across or between supply line and return line pressure. The dirt sensor valve is put into the starting operation position shown in FIG. 1 by high pressure $P_s$ via passageways 20, 21, which overcomes $P_r$ plus the springs 31, 32 and moves the valve to the left into the first position, shown in FIG. 1.

Since there is no particulate material yet collected at the silt trap, the pressure downstream of the dirt sensor valve $P_c$ is essentially supply line pressure $P_s$. This supply line pressure is communicated via the passage 10 to the upstream surface 14 of the spool valve 13, and since the pressure in chamber 18 on each side of the valve 1 is equal to $P_r$, the supply line pressure overcomes the biasing force of the spring 19, moving the toggle valve towards the left-hand first position shown in FIG. 1. As the spool valve 13 moves passage 10a is opened to pressure $P_c$, which is communicated to the area of face 11 of the piston 1a, snapping the valve into its limiting position shown in FIG. 1. At the same time, the passageways 21, 22 are put into fluid pressure communication, so that return line pressure $P_r$ is communicated to the upstream face 23 of the dirt sensor valve 2, but the valve remains stationary, in the first limiting position shown in FIG. 1, since the pressure $P_c$ downstream of the silt trap 3 is still as high as $P_s$.

A small amount of fluid, such as hydraulic fluid from the supply line 6, flows through the silt trap 3. Initially, $P_s$ equals $P_c$, on the other side of the trap, while the trap remains unblocked. However, the larger particulate material, unable to pass through the gap 3a, is trapped, and gradually accumulates in the silt trap 3, gradually restricting flow through the silt trap, and as $P_c$ decreases building up a differential pressure $\Delta P_s - P_c$ across the silt trap.

As more and more particulate material is collected at the silt trap 3, the pressure $P_c$ in lines 5 and 10 downstream of the dirt sensor valve 2 begins to decrease. Eventually, the pressure $P_c$ at face 37 of the spool valve 36 of the dirt sensor valve 2 becomes insufficient, with return line pressure equalized on each side of the valve piston 2a, to resist the biasing force of springs 31, 32, and the piston and spool valve 2 move to the right, into the second position, shown in FIG. 2. In this position, the silt trap moves into the position seen in FIG. 2, with the valve surface 37 of the valve 36 adjacent to the vent 38. In this position, the valve 36 is closed by a low clearance fit between spool 36 and end 34, permitting only a very low leakage flow past the end 34. This leakage flow carries off the silt collected in the recess 33 on end 34 into the diagnostic filter 7 where it is collected. The silt trap 33 is then empty of silt, and ready for another cycle.

The pressure $P_c$ continues to decrease, and then $P_c$ at face 14 of the spool valve 13 and face 11 of the piston 1a is no longer sufficient to overcome the combined biasing force of the spring 19 of the toggle valve piston 1a, and return line pressure $P_r$ on the downstream face 17 of the toggle valve piston 1a. The biasing force of the spring 19 overcomes the reduced pressure $P_c$ and moves the piston 1a to the right, into the second position shown in FIG. 2, closing off the passage 10a, and the communication between passages 21 and 22, while putting passages 20, 21 into communication. This feeds supply line pressure $P_s$ to the face 23 of the dirt sensor of the valve 2. The resulting differential pressure across the valve piston 2a snaps the valve piston to the left-hand first position shown in FIG. 1, in position for the next cycle.

The fact that the silt trap has been plugged is signalled by the pressure cycle counter 4, which is actuated by a predetermined low pressure in line 5b.

The cycling rate, that is, the time interval between cycles, is proportional to the density or concentration or load of the particulate material in the fluid being monitored. The device can be calibrated by measuring the contaminant load in the fluid, and then graphing the cycling interval against load. One may then read off the load from the cycling interval on the curve, to determine the load for the fluid being monitored.

Having regard to the foregoing disclosure, the following is claimed as the inventive and patentable embodiments thereof:

1. A device for determining the concentration of solid contaminants suspended in a fluid, having an orifice or narrow passage through which the fluid carrying suspended solid contaminants is passed, and monitoring the rate of build-up of the solid contaminants unable to pass through the orifice or narrow passage as a function of the concentration of the contaminants in the fluid, comprising, in combination:
    (i) a fluid inlet and a fluid outlet for attachment respectively to a system supply fluid line and system return fluid line;
    (ii) a fluid passage extending between the fluid inlet and the fluid outlet;
    (iii) a first flow restriction across the fluid passage, sized to prevent passage therethrough of solid contaminant particles to be sensed and estimated, and suspended in fluid flowing through the restriction, and collect such particles upstream thereof;
    (iv) a second flow restriction across the fluid passage, downstream of the first and controlling fluid flow through the passage and the first flow restriction to less than a selected maximum;
    (v) first valve means movable only between first and second positions, having a first pressure receiving surface selectively exposed to system return fluid pressure or to fluid pressure downstream of the first flow restriction and a second pressure receiving surface exposed solely to system return fluid pressure;
    (vi) first biasing means biasing the first valve means towards the second position against pressure downstream of the first flow restriction, the valve means being moved into the first position against the biasing means whenever fluid pressure downstream of the flow restriction is greater than system return fluid pressure; and otherwise being moved into the second position by the biasing means;
    (vii) second valve means movable only between first and second positions having first and second pressure-receiving surfaces exposed, respectively, to either system supply or system return fluid pressure, according to the position of the first valve means, and fluid pressure downstream of the first flow restrictor; and to system return fluid pressure;
    (viii) second biasing means biasing the second valve means towards the second position against system supply or system return fluid pressure and fluid pressure downstream of the first flow restriction; the valve means being moved into the first position whenever system supply fluid pressure downstream of the first flow restriction greater than system return fluid pressure is applied to the first pressure-receiving surface of the second valve means and otherwise being moved into the second position by the biasing means;
    (ix) the first valve means controlling application of system supply fluid pressure to the first pressure-receiving surface of the second valve means, and permitting such application only when in the first position; whereby the first and second valve means each are moved against their respective biasing means into their first positions while the first flow restriction remains in a relatively contaminant-unblocked condition, and whenever the flow through the first flow restriction becomes blocked by contaminants and the first flow restriction is in a relatively contaminant-blocked condition, so that the fluid pressure differential thereacross exceeds a predetermined minimum, both valve means are moved into their second positions by their respective biasing means;
    (x) means for cleaning away contaminants collected at the first flow restriction and restoring it to a contaminant-unblocked condition whenever the second valve means is in the second position; and
    (xi) means responsive to fluid pressure differential between system return fluid pressure and fluid pressure downstream of the first flow restriction for signalling each time such fluid pressure differential exceeds a predetermined minimum.

2. A device according to claim 1 in which the first and second valve means are slide spool or poppet valves, or a combination thereof, spring-biased into one of their two limiting positions, and exposed to fluid pressure on each side thereof, so as to be moved against the spring bias at a predetermined pressure differential thereacross.

3. A device according to claim 1 in which the means for signalling the contaminant-blocked condition of the first flow restriction is a differential pressure indicator arranged to give a visual signal.

4. A device according to claim 1 in which the second flow restriction can be adjusted to provide a range of flows less than but proportional to main flow in the fluid system.

5. A contaminant sensing and monitoring device in accordance with claim 1, in which the first biasing means biasing the first valve means towards the second position against fluid pressure downstream of the first flow restriction has a biasing force low enough that the valve means is moved into the first position against the biasing force whenever fluid pressure downstream of the flow restriction is approximately 80% of system return fluid pressure.

6. A contaminant sensing and monitoring device in accordance with claim 1, in which the first and second valve means each are moved against their respective biasing means at different pressure differentials thereacross so that initially the second valve means and then at a larger differential pressure the first valve means is moved into its second position.

* * * * *